United States Patent [19]

Liotta et al.

[11] Patent Number: 5,604,106
[45] Date of Patent: Feb. 18, 1997

[54] METHOD FOR DETECTING CARCINOMA

[76] Inventors: Lance A. Liotta, 9027 Mistwood Dr., Potomac, Md. 20854; Elliott Schiffmann, 3207 Pickwick La., Chevy Chase, Md. 20815

[21] Appl. No.: 62,717

[22] Filed: May 18, 1993

Related U.S. Application Data

[63] Continuation of Ser. No. 336,557, Apr. 10, 1989, abandoned, which is a continuation-in-part of Ser. No. 58,381, Jun. 5, 1987, abandoned.

[51] Int. Cl.⁶ .......................... G01N 33/574; C07K 16/24
[52] U.S. Cl. ..................... 435/7.23; 436/64; 436/813; 530/389.2; 530/389.7
[58] Field of Search ......................... 436/501, 536, 436/63, 64, 813; 435/7.2, 7.21, 7.23

[56] References Cited

U.S. PATENT DOCUMENTS

| | | | |
|---|---|---|---|
| 4,584,268 | 4/1986 | Ceriani et al. | 435/7.23 |
| 4,725,538 | 2/1988 | Senger | 435/7.23 |
| 4,921,790 | 5/1990 | O'Brien | 435/7.23 |

OTHER PUBLICATIONS

Liotta, et al., "Tumor cell autocrine motility factor", Proc. Natl. Acad. Sci. USA, vol. 83, May, 1986, pp. 3302–3306.

Stracke, et al., "Pertussis toxin inhibits stimulated motility independently of the adenylate cyclase pathway in human melanoma cells", Biochem. Biophys. Res. Commun., vol. 146, No. 1, 1987, Jul. 15, 1987, pp. 339–345.

Chodak, et al., "Partial characterization of a cell motility factor from human urine", Cancer Research, vol. 45, Feb. 1985, pp. 690–694.

Chodak, et al., "Increased levels of fibroblast growth factor–like activity in urine from patients with bladder or kidney cancer", Cancer Research, vol. 48, Apr. 15, 1988, pp. 2083–2088.

L. Liotta et al., Cancer Metastasis: Experimental and Clinical Strategies, Prog. Clin. Biol. Res., 212, pp. 17–24 (1986).

L. Liotta, et al., Anticancer Drug Des., 2(2), pp. 195–202 (1987).

R. Guirguis et al., Nature, vol. 329, pp. 261–263 (1987).

K. Atrip et al., Biochem. and Biophys. Res. Comm., vol. 146, No. 3, pp. 996–1002 (1987).

*Primary Examiner*—Mary E. Ceperley
*Attorney, Agent, or Firm*—NIH Office of Technology Transfer

[57] ABSTRACT

A new method of detecting cancer by determining the presence of autocrine motility factor (AMF) in the body fluid is described. The method utilizes induction of motility in suitable responder cells by a sample of the body fluid. If the responder cells demonstrate motility, cancer is indicated in the person from whom the body fluid was obtained.

12 Claims, 3 Drawing Sheets

METHOD FOR DETECTING CARCINOMA

This application is a continuation of U.S. patent application Ser. No. 07/336,557, filed Apr. 10, 1989, now abandoned, which is a continuation-in-part application of U.S. patent application Ser. No. 07/058,381, filed Jun. 5, 1987, now abandoned.

This is a continuation in part of the pending U.S. patent application Ser. No. 07/058,381 filed Jun. 5, 1987, which is incorporated herein by reference.

The present invention is related generally to the field of cancer diagnosis. More particularly, the present invention is related to a novel method of detecting cancer utilizing the presence of autocrine motility factor in the body fluid as an indicator of carcinoma.

Recent studies have demonstrated tumor cell motility as a major determinant of metastasis. In this respect, a tumor autocrine motility factor (AMF), a cytokine, has been identified and characterized (Liotta et al, Proc Natl Acad Sci USA 1986; 83:3302–3306). AMF is a protein of about 54 kilodaltons as determined by gel filtration and gel electrophoresis and its NH2 terminus comprises the amino acid sequence: DKELRFRDCTKSLAEANKK (single letter code). Under the influence of AMF, the cells migrate strongly both chemotactically and chemokinetically. A primary event in the initiation of a motile response is the extension of pseudopodia (Guirguis et al. Nature 1987; 829:261–263). At the biochemical level, the amplification of the signal generated by the interaction between the cell and its AMF appears to involve an obligatory role for a pertussis toxin-sensitive G-protein (Stracke et al, Biochem Biophys Res Commun 1987; 146:339–345). Based on these findings, a relatively simple, non-invasive assay of the present invention has been developed for the detection of AMF in urine as a particular marker for transitional cell carcinoma (TCC) and for urinary tract malignancies in general. The method of the present invention allows the use of AMF as a predictor of tumor progression and a detector of its recurrence at an early stage prior to performimg other conventional tests.

BRIEF DESCRIPTION OF DRAWINGS

Various objects, features and many of the attendant advantages of the invention will be better understood upon a reading of the following detailed description when considered in connection with the accompanying drawings wherein.

DETAILED DESCRIPTION OF THE INVENTION

Figure 1:
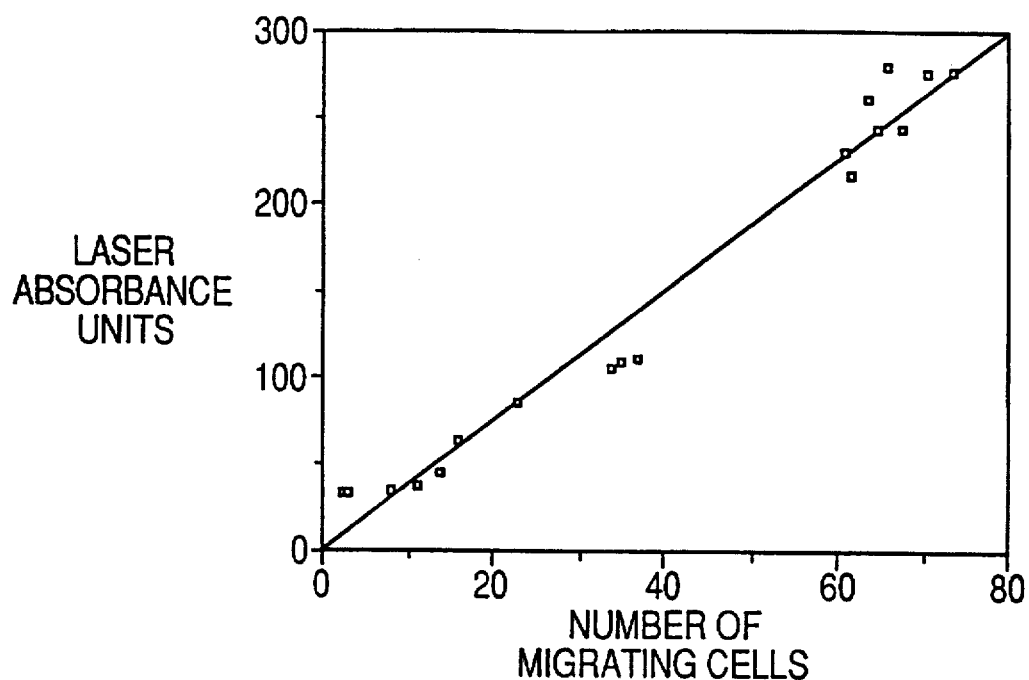
FIG. 1 is a plot of laser densitometric values as a measure of cell migration. Migration assays to different concentrations of AMF were performed in multiwell chambers. The areas of the filter that contained stained cells were subjected to a laser densitometric scan at an absorbance of 633 nm. The laser absorbance units corresponding to the number of migrated cells at a given concentration of AMF were plotted against the optically determined number of cells per high power field. From the linear correlation curve, the laser density unit can be calculated as follows: 6=31/62+3.75x, where y: optical density at 6.33 nm and x: no. cells per high power field. The S.E.M.s for each value did not exceed 10 percent.

Various objects and advantages of the present invention are achieved by a method of detecting carcinoma, comprising determining the presence of AMF in the body fluid of a subject the presence of AMF in the body fluid being indicative of the presence of carcinoma in said subject.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art. The materials, methods and examples are only illustrative and not limiting.

MATERIALS AND METHODS

Responder Cell Lines

A number of cell lines are commercially available from such sources as the ATCC, Rockville, Md., which can be used as responder cell lines for AMF assay. Cells which become motile under the influence of AMF are designated herein as the responder cells. Examples of such cell lines are human melanoma cell line (A2058), breast cancer cell lines (MDA 231 and 435), transitional cell carcinoma of the bladder (T24A and T24P), human breast adenocarelnoma (ATCC HTB 22). human breast carcinoma from pleural effusion (ATCC HTB 23), human breast medullary carcinoma (ATCC HTB 24), human breast carcinoma, brain metastasis (ATCC HTB 27), human adenocarcinoma of the colon (ATCC HTB 39), human carcinoma of the lung (ATCC HTB 53), malignant melanoma, lymph node metastasis (ATCC HTB 66 and 69), human rhabdomyosarcoma (ATCC HTB 82) and the like. Any one of these cell lines can be employed as a source of responder cells, of course with proper adjustment for background motility, etc., as is well understood by one of ordinary skill in the art. The choice of a particular cell line per se is not a part of this invention.

In the present study, the tests were conducted as a blind study where the clinical and pathologic diagnoses were not revealed to the researcher until after completion of the tests. As a check, initially three different human cancer cell lines were used to determine if the urines of TCC patients contained AMF-like activity. These responder cell lines were human melanoma cell line (A2058), breast cancer cell lines (MDA-435s and MDA-231), and transitional cell carcinoma of the bladder (T24A and T24P). The T24 cell line was quite responsive to known AMF preparations, but also had a higher background of spontaneous motility compared to the other cell lines. The other cell lines, however, had much lower background motilities, with the MDA-435s the lowest. The MDA-435s human breast cancer cell line was, therefore, used for screening patients' urines in the vast majority of the cases. However, as noted above, other cell lines could also be employed. For instance, the T24P (Flatow et al. Int J Cancer 1987; 40:240–245) cell line was also used at times because it is an authentic bladder cancer line that produces and responds to AMF. Furthermore, its response to processed urine samples matched that of the MDA-435s line (data not shown). All cultures were maintained in DMEM containing 10% fetal calf serum.

Antibody Preparation

For the preparation of murine antibodies to AMF, purified AMF (about 10 ug) was emulsified with complete Freund's adjuvant and injected into the foot pad of three C3H mice. Two weeks later the mice were boosted with 5 ug of AMF in PBS injected intravenously in the tall vein In a volume of 0.1 ml. One month later the mice were bled and the serum was tested for its ability to inhibit tumor cell motility. In this assay the mouse sera was preincubated with the AMF in the Boyden chamber migration assay. At a dilution of 1/1000 the mouse sera produced 90% inhibition of tumor cell motility compared to pooled mouse sera control.

Purified AMF protein (10 ug) was emulsified in complete Freund's adjuvant and injected into a subcutaneous site on the back of New Zealand white rabbits. Booster injections of ug were applied at 6 and 12 weeks. At 3 and 4 months the rabbits were bled and the sera was tested for motility inhibition activity. At a dose of 1/1000 the immune sera abolished motility compared to control preimmune sera. The sera were heat inactivated at 56° C. for 30 minutes.

Grade and stage of samples. Tumor grade was determined by two independent pathologists using a scale of one to three with grade one tumors showing the most differentiation and grade three the least. Bladder tumors were staged according to the American Joint Committee TNM classification (Manual for Staging of Cancer. Am. Joint Committee on Cancer, Philadelphia, 1983, B. Lippincott Co., 2nd ed., part II, pp. 23–242).

Urine samples. Twenty-four hour patient urine samples were processed as follows for determination of their AMF content. Samples were normalized by concentrating the volume of each specimen to 2 ml. The pE was adjusted to 8.8 with 1 N Tris buffer, and the solutions were agitated for 3 min (Vortex). The urine in each sample was replaced with phosphate-buffered saline (PBS) containing $CA^+$ and $Mg^{++}$ (PBS, Ca, Mg, pH 7.4) with the aid of an Amicon microconcentrator, which retained molecules of $Mr \geq 30$ KDa. The concentrates obtained in this manner (stock solutions) were stored as frozen (–70° C.) aliquots.

Serum-free conditioned medium. Two sets of five 150 cm² tissue flasks containing T24P cells that were 60% confluent were used in preparing the conditioned medium. Cells in the first set of flasks were washed twice with PBS for two min each before adding 35 ml of DMEM without serum to each flask. After a 12 hr incubation, the serum-less conditioned medium was then collected and replaced with the medium containing 10% FCS from the second set. Cells in the second set of tissue culture flasks were washed twice in the manner mentioned above, and the serum-free conditioned medium from the first set was then added (approximately 35 ml) to each flask. All media were filtered using an Amicon filtration kit with a 0.4 u filter prior to their addition to the next set of flasks. Pulsing the cells in this alternate manner was continued for 72 hr (6 pulses) before starting the cycle again with fresh cells and fresh media. The serum-free medium collected in this manner was then concentrated ten-fold, and replaced with PBS using centrifugal microconcentrators (Amicon) with a filter that retained molecules of $Mr \geq 30$ KDa.

Chemotaxis assay. Cells that were 75–90% confluent were trypsinized with trypsin-EDTA and allowed to recover at room temperature for 30 min. in DMEM containing 10% FCS. The cells were then resuspended at a concentration of $2 \times 10^6$ cells/ml in DMEM supplemented with 0.1% bovine serum albumin. Using a modified Boyden chamber, the cells were added to the upper wells of 48 micro well chambers with type IV collagen-coated Nuclepore membranes (8 um pore size) separating the upper from the lower wells (Llotta et al. Proc Natl Acad Sci USA 1986; 83:3302–3306). The attractant was added to the lower wells. Incubation of chambers was at 37° for 5 hr. All chemotaxis assays for the urine samples and controls were done in triplicate and repeated at least three times with different cell line passages. At the end of the incubation period, the filters were stained using Diff-Quick solutions (American Scientific Products) and placed on a glass slide with the upper surface of the filter exposed. The cells on the upper surface of the filter were wiped off with tissue paper. The stained cell areas on the lower surface of the filter apposed to the slide were then read with a 2202 Ultrascan Laser Densitometer (LKB) Instruments, Gaithersburg, Md.) at a wavelength of 633 nm. The density of color was proportional to the number of cells per optical field according to the equation: $y = 31.6 + 3.75 X$ (FIG. 1); X=no. cells/high power field (500X) (FIG. 1).

Inhibition of AMF-stimulated motility by antibody to AMF. Serial dilutions of antt-AMF antibodies and preimmune rabbit serum were prepared and added to aliquots using stock processed urine samples (nos. 69, 79 Table 1) and PBS. The mixtures of urine-containing motility-stimulating activity and antibody were then incubated for 30 min prior to their use in the chemotaxis assay. The assay was carried out as described above using cells of the MDA-435 human breast cancer cell line as responder cells.

Immunoblotting of urine AMF. The concentrated urine samples were electrophoresed on SDS-PAGE according to Laemmli (Laemmli U.K. Nature 1970; 227:680). After electrophoresis, transfer of proteins to nitrocellulose filters was performed in a transblot apparatus (Bio-Rad). The transfer buffer contained 20 mM Tris HCl, 150 mM glycine, and 20% (v/v) methanol. Residual binding sites on the nitrocellulose filters were blocked by incubation with 2% gelatin in PBS overnight at 57° C. Anti-AMF antibodies (polyclonal antiserum against purified AMF from A2058 human melanoma cell line) were diluted 1:100 in DMEM containing 10% FCS, 1% Tween 20 and incubated with the nitrocellulose papers for 2 hr at 37° C. with shaking. After three-10 min. washes in 50 mM Tris-HCl, 150 mM HCl, and 1% Tween 20, the nitrocellulose papers were incubated for 2 hr at 4° C. with secondary antibody (Kirkegard & Perry Laboratories, Inc.), an affinity purified goat anti-rabbit horseradish peroxidase conjugate, diluted 1:200 in 0.2% Tween 20, normal goat serum solution. The filters were washed four times in PBS for 5 min per wish before development. The developer solution contained 10 mg diaminobenzidine and 1 ul $H_2O_2$ per ml of PBS. After the color had developed, the filters were washed extensively with distilled water.

RESULTS

Figure 2:
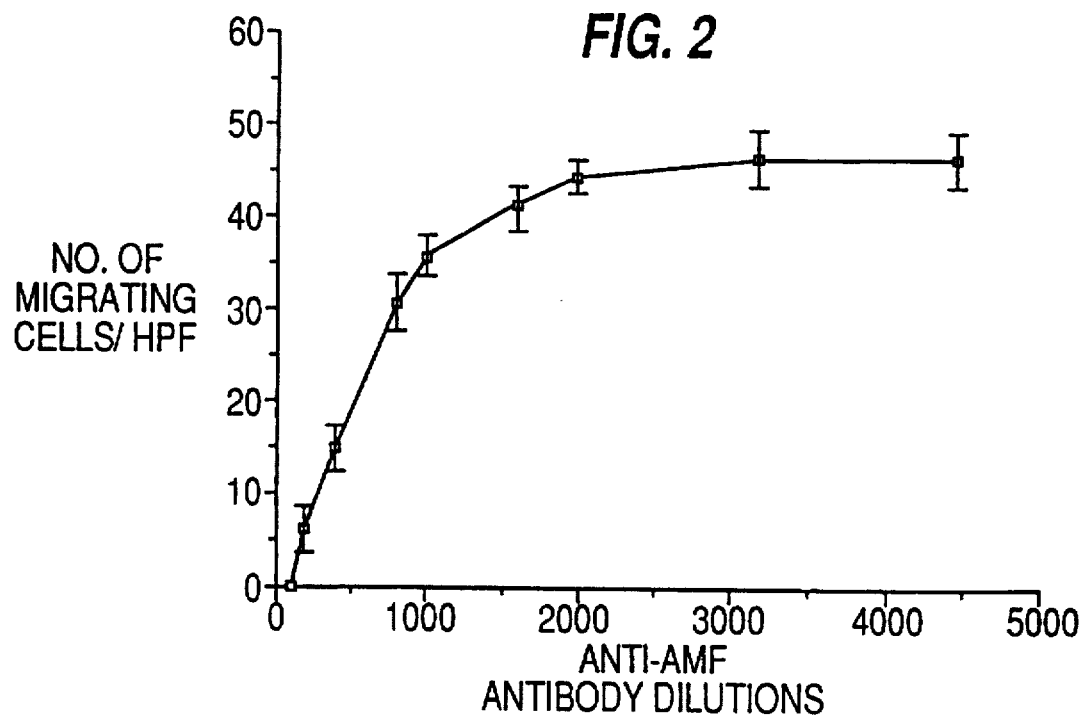
FIG. 2 demonstrates that anti-AMF rabbit serum antibodies neutralize AMF activity in the urine of TCC patients. Serial dilutions of anti-AMF rabbit serum antibodies were prepared and mixed with an aliquot of urine extract of samples #69 and #79 from patients with TCC of the bladder grade III (Table 1). The urine-antibody mixtures were preincubated for 30 min prior to the chemotaxis test in which the MDA-435s human breast cancer cell line was used as responder cells.

Inhibition of AMF-stimulated motility by antibody to AMF. A polyclonal antibody to the AMF produced by A2058 human melanoma cells was added in progressive dilutions to AMF preparations from the urines of patients (#69, 79, Table 1) diagnosed for stage III transitional cell carcinoma. With the use of the MDA-435s breast carcinoma line as responder cells to a maximally stimulating concentration of the urinary AMF preparation, a dose-dependent inhibition of stimulated motility was observed in the presence of the IgG fraction of the anti-body to AMF (FIG. 2). As a control, pre-immune rabbit serum had no effect (not shown). There would appear, then, to be common domains on AMF obtained from melanoma cells and obtained from urine of patients with TCC. From these results, it became clear that an ELISA procedure could be employed to quantitate the presence of AMF from urine.

Figure 3:
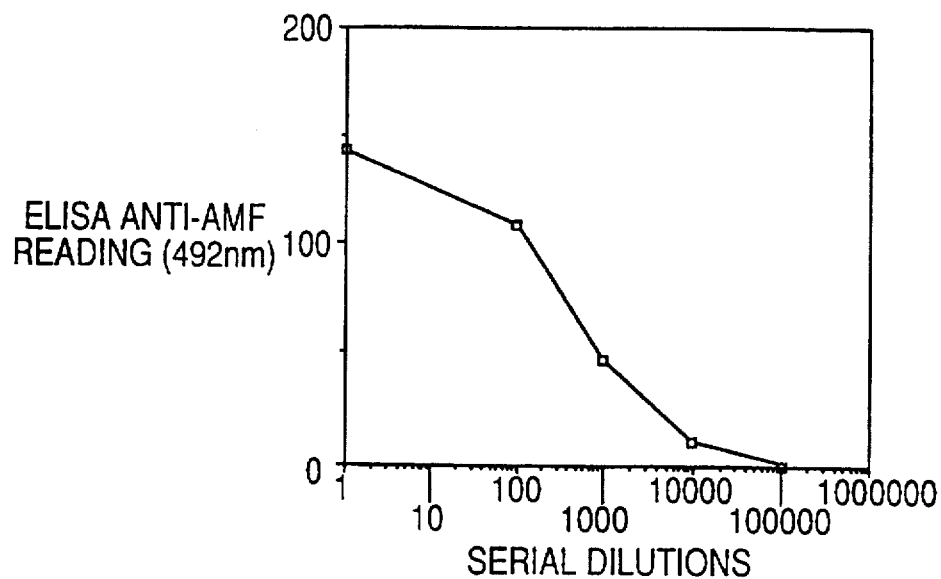
FIG. 3 shows anti-AMF ELISA standard curve (serial dilutions) of TCC grade III urine sample. Using a sample of TCC patient urine (sample #69), an ELISA was performed on serial dilutions of the melanoma anti-AMF IgG fraction. The Intensity of absorbance at 492 nm was found to be quantitatively related to the amount of antibody reacting with the concentrated sample of urinary AMF.

ELISA for AMF from urine. Using a sample of TCC patient urine #69 that had been concentrated 100x, an ELISA was performed on serial dilutions of the melanoma AMF antibody. It was found that the intensity of absorbance at 492 nm is proportional to the amount of antibody reacting with a concentrated sample of urinary AMF (FIG. 3). These results indicated that the ELISA method, In addition to the motility assay, can also be used to quantitate AMF in body fluids, such as urine.

Determination of the AMF content of 24-hour urine samples from patients with benign and malignant tumors. The AMF content of patient and control urine samples was compared by measuring the motility response in responder cells produced by processed aliquots of each patient's urine. Also determined was the AMF content by the ELISA procedure (Table 1). Aliquots of these samples were tested for their ability to stimulate motility in the multiwell chamber. The motility responses on the linear portion of the concentration-activity curve for the migrating cell was used to calculate AMF activity for each sample. These were then normalized to compare the AMF activity of each sample. The motility values in Table 1 are given as laser-densitometric units from the optical scan of stained cells migrating to patient samples, normal or non-cancerous patient samples, and to a PBS control. The urines of 34 of 36 patients with normal or benign conditions, as determined by pathologic diagnosis, had motility values not exceeding 100. ELISA readings were undetectable for 21 out of 24 of these samples and did not exceed a value of 11 for the rest of this group except for sample #109 (see below). Urines from patients #76 and #116 gave motility values greater than 100, within the range of those found for urine of bladder cancer patients. However, the ELISA readings were not confirmatory. In the cases of 23 patients of the initial group (Table 1) with known transitional cell carcinoma (TCC) disease, the motility values exceeded 100 in all cases except two, and these (#77, 108) were in the low grade (I) of disease.

It should be noted that in the eases of two patients (#83, #112) whose initial diagnoses were malignant, their urinary motility values were 35 and 14 respectively, indicating very low levels of AMF. Upon a follow-up examination, the diagnoses were changed to indicate the absence of TCC. In the case of patient #82, the initial pathologic diagnosis was negative, with failure to find a neoplasm upon biopsy. However, the patient's urine contained an appreciable AMF response (200 units) indicating the presence of a malignancy. Upon repeated examination, the biopsy was indeed positive, confirming the implication of the urinary AMF content determined prior to surgery.

Figure 4:
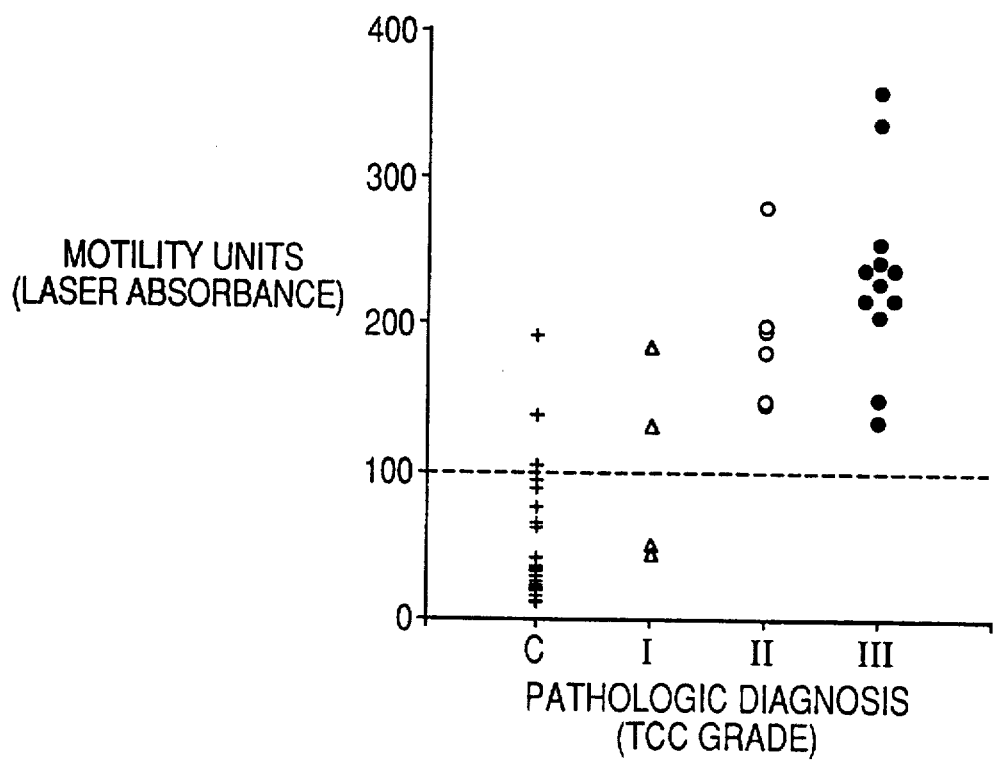
FIG. 4 shows the motility Values obtained for urines from TCC patients and controls. The latter category included both normals and those with non-malignant conditions. The means and P values distinguishing each group from the others are shown in Table 3. Confidence intervals for both malignant and control categories indicated that a motility value of 100 (dotted line) could best distinguish between the two categories (C.I. ≧95): motility values of 32 of 36 controls fall below the dotted line, whereas 20 out of 23 of the TCC values were above the line.

These results indicate that AMF quantitation of urine samples is a valuable method of grading bladder cancer in its early phase. The average motility values for urines from the benign conditions, on the one hand, and for urines from each of the three transitional carcinoma classes, on the other hand, are clearly different and progressively greater with each stage of disease severity (FIG. 4). The ELISA method of quantitating AMP content gave values for patient urine samples that correlated very well with the final diagnosis with smaller SEMs than those of the motility values. It has also been found (Table 1, Motility Value Data Summary) that the motility assay could reliably distinguish not only between malignant and non-malignant conditions (including normals) but also between non-invasive and invasive TCC. These findings demonstrate the value of the assay of the present invention as a predictor for the course of the disease.

Figure 5:
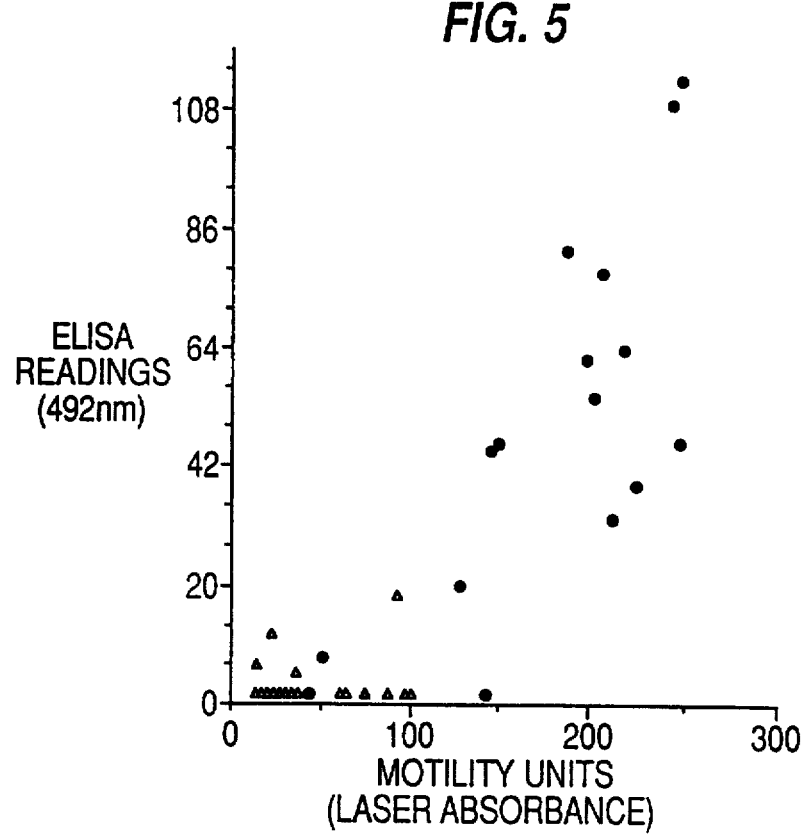
FIG. 5 shows the measured AMF content (ELISA values) vs AMF biological activity (motility units) in the urines of TCC patients and controls. The biological activity of AMF (motility) and its content (anti-AMF ELISA) were measured in the urine samples of 16 out of 23 patients (0) and 24 out of 27 controls (▲) from Table 1. The vast majority of the control motility values were below 100 (laser absorbance units) except for 4 out of 36 cases (Table 1) where the ELISA values were below 20. However, all measured ELISA values of TCC urines grade II and III were significantly higher.

Grading of bladder cancer and AMF determination in patients' urines. The histologically determined grades of bladder cancer were grouped by the migratory response of cells to the AMF content from urine of the patients in each grade of TCC (FIG. 4), as well as by the concentration of urinary AMF as determined by ELISA (FIG. 5). It was found that there was an increasing level of AMF in urines of patients with advancing grade of the disease. Urine from benign conditions produced the lowest relative motility. In fact, combination of both the direct motility determinations and the ELISA method appeared to increase the accuracy in distinguishing between malignant and non-malignant categories. The vast majority of the control motility values were below 100, but all the control ELISA values, including the 'aberrant' ones giving greater than 100 motility values, were ≦20.

Figure 6:
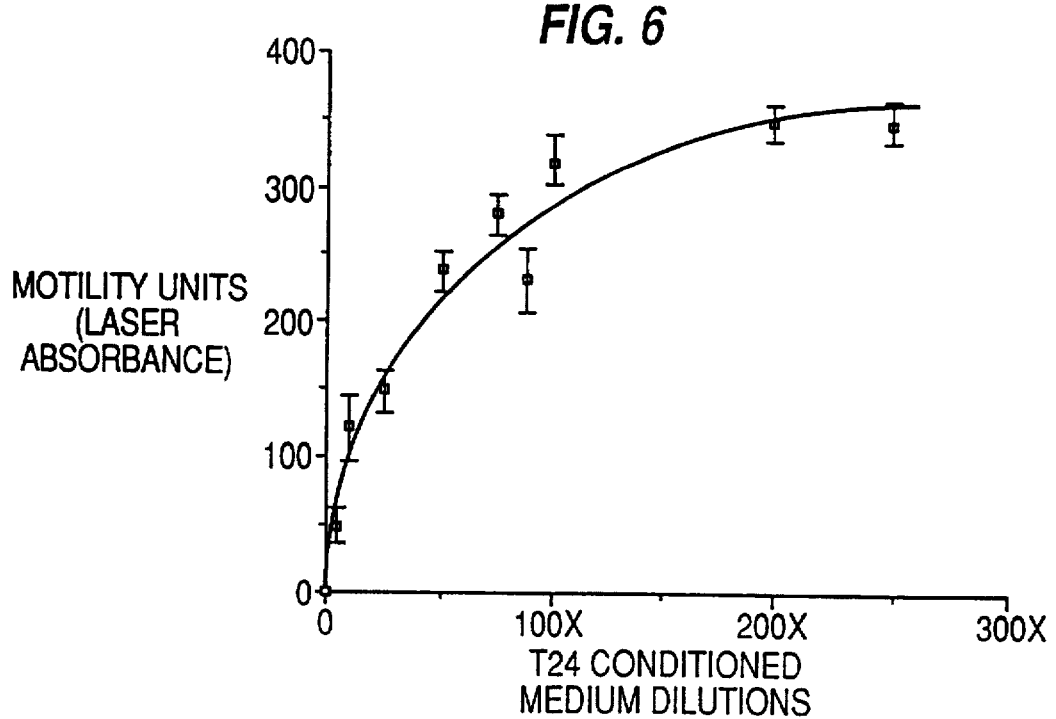
FIG. 6 shows the TCC cell line (T24P) dose response to its own serum-free conditioned medium. T24P cells (Chodak et al. Cancer Res 1985; 45:690–694) were grown in serum-free media. The media were concentrated 200 fold and diluted with fresh medium to give a series of concentrations. These cells showed a dose-dependent motile response to their own conditioned medium. These findings allowed the use of the T24P cell line as a source of responder cells in subsequent tests (Table 2).

Autocrine motility response of cells from bladder cancer. The occurrence of motility factors in patient urine could result from tumors originating in areas other than the urinary tract. It was, therefore, considered important to demonstrate that a human bladder cancer cell could produce and respond to its AMF. T24P cells were grown in serum-free media. The media were concentrated 250-fold and diluted with fresh medium to give a series of concentrations. These cells showed a dose-dependent motile response to their own conditioned medium (FIG. 6). These findings permitted the use of the T24P cell line as a source of responder cells in subsequent tests.

Motility as indicator of disease status of 'follow-up' patients. Table 2 lists the follow-up diagnoses and urine motility values for patients who had operative procedures to treat their transitional cell carcinomas. Patients 5, 6, 9, 10, 21 and 22 were all diagnosed to have recurrent TCC, and their urines had corresponding motility values greater than 100. Patients 4 and 7 were diagnosed to be free of cancer with a motility of less than 100. Patient 8 developed abnormal cytology with a motility value also greater than 100. Thus the motility values were generally in accord with the follow-up diagnosis after surgery. The results from these follow-up studies demonstrate that the presence of AMF in a patient's urine has an accurate prognostic significance. Table 2 also lists the pathologic diagnoses of new patients and their urinary AMF determinations using the T24P cell line as responder cell. A complete agreement was found between the pathologic diagnostic procedure and the results of the method of measuring urinary AMF. These results are summarized in the Motility Value Data Summary in Table 2. It is clear that the motility assay reliably distinguishes between tumor-free and recurrent TCC conditions in follow-up studies of patients.

The data presented herein clearly establish that AMF is found in the urine of patients with bladder cancer and the AMF content is correlated with the grading of the disease by the usual histological procedures. An antibody to AMF from human melanoma cells was also found to neutralize the motility-stimulating activity Prom TCC urine, suggesting similarity between active sites in both TCC and melanoma AMFs. The availability of this antibody made the development of an ELISA analysis feasible for urine samples of patients with TCC. Furthermore, the ELISA was found to be correlated with the results of the direct motility assay indicating a functional relationship between the antigen and the motility stimulation. The studies also indicated a correlation between the amount of AMF and the degree of invasiveness of the tumor (Table 1). Additionally, the finding that the motility assay could be reliably used to distinguish between tumor-free and TCC conditions in the follow-up study (Table 2), even though the patient sample size was small, underscores the value of AMF as a potential marker for bladder cancer. Tumor volume (data not shown) did not have any influence on the amount of AMF present in the urine of these patients when compared to the degree of invasiveness of such tumors. Although in many instances inflammatory conditions are usually associated with this type of cancer, urines from patients with chronic inflammation of either the bladder (cystitis) or the prostate (BPH) did not contain any appreciable motility-stimulating response (Table 1). Furthermore, AMF isolated from melanoma cell line did not attract leukocytes (Liotta, supra) while serum-free conditioned medium of fMLP stimulated leukocytes did not stimulate migration of tumor cells when tested in the chemotaxis assay (data not shown).

In short, the assays of the present invention provide a reliable means of diagnosing and prognosticating carcinomas by the analysis of the body fluid of the patient suspected of cancerous tumor.

It is understood that the examples and embodiments described herein are for illustrative purposes only and that various modifications or changes in light thereof will be suggested to persons skilled in the art and are to be included within the spirit and purview of this application and scope of the appended claims.

TABLE 1

Diagnosis vs. AMF biological activity and anti-AMF ELISA in 51 patients' urines and controls

| No. | Sex | Age | Clinical Diagnosis | Pathologic Diagnosis | Rel. motility[1,2] (Laser abs. units) | ELISA[3] |
|---|---|---|---|---|---|---|
| 105 | F | 38 | Bladder lesion | Leiomyoma of bladder | 23.00 ± 12 | 0 |
| 118 | M | 75 | Keratosis | Seborrheic keratosis of skin of back | 63.00 ± 41 | 0 |
| 100 | M | 53 | Bladder neck const. | Fibromuscular hyperplasia of prostate | 18.00 ± 15 | 0 |
| 78 | M | 31 | Normal (control) | Normal | 21.00 ± 9 | 11 ± 2 |
| 93 | M | 53 | Normal (control) | Normal | 64.00 ± 36 | 0 |
| 94 | M | 35 | Normal (control) | Normal | 36.00 ± 14 | 0 |
| 95 | M | 27 | Normal (control) | Normal | 23.00 ± 13 | 0 |
| 70 | M | 65 | Microhematur. | Normal | 15.00 ± 8 | — |
| 71 | M | 56 | Stone | Urinary calculus | 37.00 ± 16 | — |
| 72 | M | 33 | Stone | Urinary calculus | 42.00 ± 13 | — |
| 75 | M | 63 | Stone | Urinary calculus | 100.00 ± 57 | 5 ± 0.8 |
| 76 | M | 69 | Stone | Urinary calculus | 104.00 ± 71 | 4 ± 0.6 |
| 85 | M | 56 | Stone | Left ureteral calculus | 28.00 ± 9 | 0 |
| 83 | M | 61 | Ca. of bladder | Focal simple hyperplasia of bladder with chronic inflammation | 35.00 ± 3 | 0 |
| 112 | F | 62 | Ca. of bladder | Mild papillomatous pattern without atypia | 14.00 ± 1 | 0 |
| 102 | M | 47 | Tear medial meniscu. | Knee surgery | 15.00 ± 1 | 0 |
| 84 | M | 69 | BPH | Fibroadenomatous hyperplasia of prostate with focal chronic prostatitis | 30.00 ± 2 | 0 |
| 86 | M | 66 | BPH | Glandular and fibromuscular hyperplasia of prostate | 31.00 ± 19 | 0 |
| 90 | M | 66 | BPH | Nodular hyperplasia of prostate | 38.00 ± 16 | 0 |
| 103 | M | 66 | BPH | Glandular and fibromuscular hyperplasia of prostate | 15.00 ± 15 | 0 |
| 104 | M | 63 | BPH | Nodular hyperplasia of prostate | 77.00 ± 5 | 0 |
| 106 | M | 61 | BPH, urinary retent. | Cystic and glandular hyperplasia of prostate, chronic inflammation | 67.00 ± 7 | 0 |
| 107 | M | 73 | BPH | Nodular hyperplasia of prostate | 25.00 ± 21 | 0 |

TABLE 1-continued

| | | | | | | |
|---|---|---|---|---|---|---|
| 114 | M | 72 | BPH | Stromal and glandular hyperplasia of prostate | 90.00 ± 39 | 0 |
| 115 | M | 58 | Bladd. outlet obst. | Stromal and glandular hyperplasia of prostate | 94.00 ± 22 | 0 |
| 116 | M | 75 | Rec BPH | Glandular and stromal hyperplasia of prostate, focal cystitis | 139.00 ± 26 | 0 |
| 119 | M | 62 | BPH-urinary retent. | Nodular hyperplasia of prostate | 34.00 ± 2 | 0 |
| 109 | M | 71 | Bladder tumor | Inverted papilloma of the glandular type | 193.00 ± 6 | 19 ± 2 |
| 77 | M | 61 | Rec. bladder tumor | Grade I papillary transitional cell carcinoma with invasion of lamina propria but without invasion | 52.00 ± 2 NI | 7 ± 1 |
| 108 | M | 79 | Bladder tumor | Grade I transitional cell carcinoma without invasion | 45.00 ± 18 NI | 0 |
| 432 | F | 81 | Bladder tumor | Transitional cell carcinoma, grade II, without invasion | 132.00 ± 8 NI | 21 ± 3 |
| 73 | M | 24 | Rec bldd. tumor TCC[4] | Grade I–II papillary transitional cell carcinoma with invasion of lamina propria with cystitis | 185.00 ± 9 | 83 ± 5 |
| 82 | M | 67 | Rec. bldd. tumor TCC | Grade II papillary TCC with invasion of lamina propria | 196.00 ± 72 | 63 ± 4 |
| 88 | F | 78 | Rec. bldd. tumor TCC | Grade II papillary TCC with invasion to the submucosa | 147.00 ± 7 | 46 ± 3 |
| 91 | M | 69 | Rec. TCC pelvic mass | Grade II papillary transitional cell carcinoma without lamina propria invasion | 147.00 ± 91 NI | — |
| 588 | F | 74 | Urinary retention | Transitional cell carcinoma, grade II noninvasive | 149.00 ± 63 NI | — |
| 587 | F | 54 | Bladder tumor | Transitionial cell carcinoma, poorly differentiated, with multiple lymph node metastases | 281.00 ± 102 | — |
| 92 | M | 74 | Rec. TCC/high grade | Mild focal chronic inflammation | 200.00 ± 64 | 56 ± 7 |
| 484 | M | 70 | Bladder tumor | Transitional cell carcinoma, grade II, non-invasive (recurrent) | 137.00 ± 10 NI | — |
| 69 | M | 66 | Bladder ca. | Papillary transitional cell carcinoma, grade III, with submucosa invasion and lymphatic invasion | 244.0 ± 125 | 114 ± 8 |
| 87 | M | 60 | Bladder ca. | Metastatic grade III transitional cell carcinoma with lamina propria invasion and lymph node metastases | 203.00 ± 28 | 79 ± 6 |
| 89 | M | 69 | Ca. of bladder | Metastatic transitional cell carcinoma to prostatic urethra | 151.00 ± 49 | 47 ± 1 |
| 97 | F | 72 | Rt. uretral mass | Transitional cell carcinoma, grade III, with invasion into muscle and metastases to peri-uretral (rt) space | 215.00 ± 98 | 65 ± 12 |
| 98 | F | 59 | Bladder cancer | Transitional cell carcinoma, grade III, with invasion into muscularis and lymphatic invasion | 223.00 ± 15 | 40 ± 4 |
| 99 | M | 69 | Bladd. ca. grade III | Transitional cell carcinoma, grade III, with invasion of perivesicular fat; and metastases to right periureter | 246.00 ± 76 | 48 ± 8 |
| 110 | M | 63 | Ca. of bladder | Transitional cell carcinoma, grade III, with perivesicular invasion and metastases to lymph nodes | 211.00 ± 45 | 34 ± 3 |
| 503 | M | 75 | Rec. TCC | Transitional cell carcinoma, grade III, with vascular invasion and no metastases | 360.00 ± 153 | — |
| 533 | M | 71 | Rec. TCC | Transitional cell carcinoma, poorly diff. grade III, superficial and invasive through bladder wall into perivesicular fat - prominent vascular invasion | 339.00 ± 27 | — |
| 543 | M | 75 | Rec. TCC | Papillary transitional cell carcinoma, grade III (recurrent), invasive to muscular layer | 239.00 ± 66 | — |
| 79 | M | 67 | Bladder tumors | Papillary transitional cell carcinoma, grade II, without invasion | 239.00 ± 57 NI | 110 ± 9 |
| 74 | M | 77 | TCC/CIS | Carcinoma in situ | 182.00 ± 24 NI | |

Motility Value Data Summary

| Sample Type | | | TCC Class | | |
|---|---|---|---|---|---|
| Variable | All non-malignant | All TCC | Variable | TCC non-invasive | TCC invasive |
| mean motility | 47.33 | 197.31 | mean motility | 135.37 | 229.33 |
| std. deviation | 33.55 | 77.05 | std. deviation | 63.6 | 60.04 |
| no pts. | 27 | 22 | no pts. | 8 | 15 |
| t-statistic | −9.12 | | t-statistic | −3.50 | |
| | 47 | | degrees of freedom | 21 | |
| | <.001 | | p value | 0.002 | |

[1]Laser (absorbance unit) = (31.6187) + (3.7483) × (No. of migrating cells) . . . with correlation coefficient of 0.99
[2]All chemotaxis experiments were done in triplicates and repeated at least three times using MDA-435s cell line as responder cells
[3]ELISA reading was done at 492 nm
[4]TCC — Transitional cell carcinoma

TABLE 2

Diagnosis vs. AMF biological activity - Patient's follow up and controls

| No. patient status | Rel. motility (prior to pathologic diag.)[1,2] using T24P cell line as responder cells | Pathologic diagnosis |
|---|---|---|
| 4 S/P treatmemt for TCC[3] | 80 ± 10 | Tumor free |
| 5 S/P treatment for TCC | 210 ± 6 | Recurrent TCC |
| 6 S/P treatment for TCC | 320 ± 87 | Recurrent TCC |
| 7 S/P treatment for TCC | 70 ± 11 | Tumor free |
| 8 S/P treatment for TCC | 160 ± 32 | Abnormal cytology |
| 9 S/P treatment for TCC | 270 ± 51 | Recurrent TCC |
| 10 S/P treatment for TCC | 210 ± 62 | Recurrent TCC |
| 21 S/P treatment for TCC | 190 ± 28 | Recurrent TCC |
| 22 B/P treatment for TCC | 223 ± 24 | Recurrent TCC |
| Urine screen | | |
| 1 | 190 ± 20 | TCC-II |
| 2 | 264 ± 82 | TCC-III |
| 3 | 167 ± 38 | TCC-II |
| 11 | 33 ± 10 | Cystitis |
| 12 | 41 ± 1 | Cystitis |
| 14 | 86 ± 27 | Renal stone |
| 15 | 94 ± 33 | BPH |
| 16 | 67 ± 4 | BPH |
| 17 | 59 ± 11 | None (asymptomatic control) |
| 18 | 89 ± 15 | BPH |
| 19 | 92 ± 13 | BPH |
| 20 | 78 ± 21 | None (asymptomatic control) |

Motility Value Data Summary

| Variable | TCC | Tumor Free |
|---|---|---|
| mean motility | 228.2 | 71.7 |
| std. deviation | 51.8 | 20.3 |
| no pts. | 9 | 11 |
| t-statistic | 9.22 | |
| degrees of freedom | 18 | |
| p value | <.001 | |

[1] Rel. motility values were measured using laser absorbance units (see methods)
[2] All experiments were done in triplicates and repeated at least three times using T24P cell line as responder cells
[3] TCC — Transitional cell carcinoma

What is claimed is:

1. A method for detecting the presence of carcinoma in humans comprising reacting human body sample from a patient suspected of having carcinoma with anti-AMF antibody, a positive immunological reaction being indicative of the presence of carcinoma in said patient.

2. The method of claim 1, wherein said human body sample comprises urine from said patient.

3. The method of claim 1, wherein said reacting step comprises an enzyme-linked immunosorbent assay ("ELISA").

4. The method of claim 1, wherein said carcinoma is cancer of the urinary tract.

5. The method of claim 1, wherein said carcinoma is bladder cancer.

6. The method of claim 1, wherein said carcinoma is transitional cell carcinoma.

7. The method of claim 4, wherein said human body sample comprises urine from said patient.

8. The method of claim 4, wherein said reacting step comprises an enzyme-linked immunosorbent assay ("ELISA").

9. The method of claim 5, wherein said human body sample comprises urine from said patient.

10. The method of claim 5, wherein said reacting step comprises an enzyme-linked immunosorbent assay ("ELISA").

11. The method of claim 6, wherein said human body sample comprises urine from said patient.

12. The method of claim 6, wherein said reacting step comprises an enzyme-linked immunosorbent assay ("ELISA").

* * * * *